United States Patent [19]

Hofmann

[11] Patent Number: 4,614,109

[45] Date of Patent: Sep. 30, 1986

[54] METHOD AND DEVICE FOR TESTING THE PERMEABILITY OF MEMBRANE FILTERS

[75] Inventor: Frieder Hofmann, Kriftel, Fed. Rep. of Germany

[73] Assignee: Brunswick Corporation, Skokie, Ill.

[21] Appl. No.: 754,583

[22] Filed: Jul. 15, 1985

Related U.S. Application Data

[63] Continuation of Ser. No. 562,961, Dec. 19, 1983, abandoned.

[30] Foreign Application Priority Data

Dec. 27, 1982 [DE] Fed. Rep. of Germany ....... 3248185
Aug. 31, 1983 [DE] Fed. Rep. of Germany ....... 3331419
Aug. 31, 1983 [DE] Fed. Rep. of Germany ....... 3331420

[51] Int. Cl.⁴ ............................................ G01N 15/08
[52] U.S. Cl. ....................................................... 73/38
[58] Field of Search .................................... 73/38, 40

[56] References Cited

U.S. PATENT DOCUMENTS 3,336,793 8/1967 Tuttle ...................................... 73/40
4,384,474 5/1983 Kowalski ................................ 73/38
4,385,517 5/1983 Sorce et al. ............................ 73/38
4,449,392 5/1984 Huschke .............................. 73/38 X

OTHER PUBLICATIONS

Brock, T. D. *Membrane Filtration: A User's Guide & Reference Manual*, Science Tech, Inc., pp. 134–135, 1983.

Olson, W. P. *A System for Integrity Testing of Disc and Cartridge Membrane Filters*, In Pharm. Tech., vol. 6 (5), 1982, pp. 42–52.

Primary Examiner—Stewart J. Levy
Assistant Examiner—Joseph W. Roskos
Attorney, Agent, or Firm—James S. Waldron

[57] ABSTRACT

The invention pertains to a method and device for testing the permeability of membrane filters by submitting a wetted membrane filter on its inlet side to a predetermined testing gas pressure within a first closed system and by measuring pressure variation over time within the closed system. The object of the method of the invention is a sensitive testing method permitting permeability, and thus pore size, of a membrane filter to be determined exclusively by measurements performed on the inlet side of the membrane filter. Such measurement is performed by measuring a pressure differential with respect to a reference pressure, or by measuring the quantity of gas per unit of time flowing with respect to a reference pressure system, or else by measuring the pressure differential twice and draining, during the second measurement, a predetermined quantity of gas from the space being tested.

16 Claims, 6 Drawing Figures

METHOD AND DEVICE FOR TESTING THE PERMEABILITY OF MEMBRANE FILTERS

This is a continuation of application Ser. No. 562,961, filed Dec. 19, 1983, now abandoned.

DESCRIPTION

This invention pertains to a method permitting the permeability of membrane filters to be tested by subjecting, within a first closed system, a wetted membrane filter on its intake side to a predetermined testing gas pressure and by measuring, over time, the pressure differential occurring within said closed system.

Membrane filters are increasingly relied upon for sterilizing liquids whenever heat sterilization is impossible, e.g. because of damage to the liquid itself. By way of example, the pore size of such filters might be approximately 0.2 $\mu$m, and the pore density may be approximately $4 \times 10^9$ pores per square centimeter.

In order to test the integrity of this type of membrane filter and to verify the fact that there are no pores having a size exceeding a certain predetermined limit, wetted membrane filters are subjected to bubble-point or gas-diffusion testing. Bubble-point testing of membrane filters in a filter housing is normally done by creating a head of gas pressure on the inlet side of the membrane filter to be tested, and thus a pressure differential across said membrane filter. One end of a tube is connected to the outlet side of the filter housing of said membrane filter, the other end of the tube is submerged in a liquid contained in a vessel. In this test method, gas pressure on the inlet side of the membrane filter is gradually increased, which causes more and more gas to permeate through the filter as the pressure keeps mounting. Initially, the rate of gas flow measured on the outlet side is proportional to the increasing gas pressure on the inlet side. As soon as the rate of gas flow measured on the outlet side of the membrane filter increases at a greater rate than does the gas pressure on the inlet side—as indicated by a substantial increase in the quantity of gas bubbles escaping—the bubble point has been reached. However, the visual determination of this point must be performed subjectively; thus, it is subject to a relatively high degree of imprecision.

Gas diffusion testing is performed in practically the same manner except that, in any individual case, the gas quantities permeating through the membrane filter are collected within an up-ended graduated cylinder filled with liquid for the purpose of measuring the gas quantity penetrating the membrane filter per unit of time. It is true that this gas-diffusion, or forward-flow, test is more precise; however, the procedure is more complicated. A constant pressure is applied across a wetted membrane filter and actual flow of gas on the outlet side of the membrane filter is measured by determining the rate of flow of the water displaced from the graduated cylinder. In principle, gas diffusion is measured across a continuous layer of water as represented by the wetted membrane. The quantity (J) of gas diffusing is proportional to the pressure differential ($\Delta p$) occurring between inlet and outlet sides, and inversely proportional to the thickness (d) of the water layer or membrane; reduced to a formula:

$$J \sim \Delta p / d$$

For diffusion testing, the pressure applied on the inlet side are lower than those at which the so-called bubble point is reached. The pressures used here are normally approx. 80% of those attained during bubble-point testing.

Both processes described above are subject to the serious drawback that testing the permeability of the membrane filter implies measurements on the outlet side of the filter, thus creating the quite serious danger of causing, in the event of sterile filtration, secondary impurities on the sterile side. This is the reason why pharmacists manufacturing or using any filter will refrain from testing the system subsequent to its having been sterilized or, if testing is required nevertheless, will have to rely on a very insensitive testing method to be performed on the inlet side. This method consists in automatically increasing the pressure prevailing within the space on the inlet side of the membrane filter up to a predetermined testing gas pressure within the so-called diffusion range, below the pressure prevailing at the bubble point. As soon as the testing gas pressure has been reached, all valves on the inlet side are closed, and any changes in the gas pressure prevailing on the inlet side of the membrane filter are monitored by means of a recorder. However, this process is highly insensitive; therefore, only serious system damage, such as any leaking O rings, can be identified with it. Owing to this lack of sensitivity inherent in the so-called pressure keeping or pressure decay test, bubble point testing from the inlet side is also performed. To do so, testing gas pressure levels are increased until the pressure drop per unit of time becomes more than proportional. However, this test method has likewise been found to be highly insensitive. Tests run in parallel—determining the bubble point from the inlet side, and determining the bubble point according to the visual method described above and characterized by observing gas bubbles having passed the membrane filter—demonstrated that values obtained by employing the inlet side bubble point test method are at least 0.2 bar greater than those found when bubble points are determined by visual methods. Nevertheless, numerous pharmacists are still using this method since it is the best one currently available if integrity and permeability of a sterile membrane filter is to be checked.

Another method which is known to the art, permits the integrity and permeability of any membrane filter to be tested exclusively from the inlet side. It is true that this process permits changes in pressure on the inlet side to be determined far more precisely, however, with this method, pressures applied on the inlet side are all below 1 bar. For this reason, the method is subject to the drawback that in view of the low test gas pressures on the inlet side of the membrane filter, no reliable information as to integrity or actual permeability of any filter can be derived because, at pressures below 1 bar, test results for membranes having unacceptably high permeability values cannot be distinguished from those for membranes of admissible permeability. This means that even if there is one, or possibly even several pores the size of which are greater than admissible values, these pores will not become noticeable as their effects will be drowned out among the huge number of standard-sized pores—around $10^9$ per square centimeter—since the bubble point of any such standard-sized pore has not yet been exceeded.

A practical example will explain how small the pressure differentials due to diffusion losses are on the inlet side of the filter housing. On the inlet side, the volume of a 250 mm filter housing will at best be approximately 1000 ml; thus, the maximum diffusion pressure differential will be 6 mbar/min if $N_2$ diffusion through the wetted membrane of the filter cartridge amounts to approximately 6 ml/min for a 2.5 bar testing pressure. However, a very slight increase in the amount of gas passing through the filter indicates that the filter is leaking. This is why pressure differentials have to be determined by methods which are as sensitive and as precise as possible. Electronic averaging of measured values obtained with a single pressure transducer will permit, at relevant testing pressure levels, no more than a 1 or 2 mbar resolution, resulting in a correspondingly high lack of precision as regards absolute values.

It is the object of this invention to present a testing method which is as sensitive as possible and which permits the permeability, and thus the pore size, of a membrane filter to be determined exclusively by measurements performed on the inlet side of said membrane filter.

According to the invention and based on a method of testing the permeability of membrane filters of the kind mentioned initially, this object is achieved by bringing up, at the beginning of any measurement, a reference pressure system to the testing gas pressure and by measuring the change in pressure by way of obtaining the pressure differentials between the first system and said reference pressure system.

For one thing, this method is characterized by the advantage that measurements can be perfomed at relatively high testing gas pressures, i.e., directly below or even at the bubble point which may mean, by way of example, absolute pressure of between 2.5 and 3.5 bars; this is what really permits distinguishing between membrane filters having admissible permeability and those subject to unacceptable values. Another important advantage of this method consists in the fact that, despite this high level of absolute pressures, values measured for pressure gradients within the space on the inlet side of the membrane filter can be made substantially more sensitive and precise by measuring the differential between the pressure prevailing within the system on the inlet side of the membrane filter and the one obtaining within the reference pressure system. According to the invention, sensitivity and precision values of approximately 0.1 mbar can be achieved irrespective of testing pressure levels. This means that measuring sensitivity has been improved substantially. Measurements as such can be performed exclusively on the inlet side.

The testing method will preferentially be performed so as to link, prior to any measurement, a first system and reference pressure system, separating them whenever a measurement is initiated. This permits the testing gas pressure to be determined and read off only once prior to any measurement; moreover, the procedure ensures that at the beginning of any test the pressure level prevailing within the reference pressure system is identical to the level of pressure tested within the measuring system. Whenever any test is initiated, it will be sufficient to simply separate the first system and said pressure reference system.

The pressure reference system may of course be connected directly to the source of gas pressure, and be brought up independently from the measuring system proper to any predetermined testing gas pressure. Even in this case, the reference pressure system ought to be separated from said source of gas pressure at the beginning of any measurement so as to preclude the subsequent occurrence of pressure variations due to, say, changes in temperature.

Since the pressure measuring system is extremely sensitive, testing it first for its integrity will be indicated in order to prevent pressure measuring equipment from being damaged by rapid loss of pressure through possible leaks. For pretesting the integrity of the membrane filter, it will be preferable to connect the first system and the reference pressure system and to bring them up to a predetermined test gas pressure prior to measuring the loss of pressure for the entire system. In this manner, no pressure variations will reach the sensitive measuring equipment used to measure the pressure differential prevailing between the first system and reference pressure system so that it will be protected against being damaged. Only if the system has been found to contain no major leaks, can the testing process proper be performed.

This invention relates, moreover, to a device permitting the testing method to be performed, which device is characterized in that the space on the inlet side of the membrane filter is connected, via a line and a pressure control valve, to a source of gas pressure, in that a first pressure measuring device is provided with a bypass to said line connecting the pressure control valve and the space on the inlet side, and in that within said bypass line is a shut-off valve permitting a reference pressure system, capable of being insulated, to be formed between the shut-off valve and the pressure measuring device.

Since the precision of the measurements is particularly subject to temperature variations within the measuring system, it will be preferable to control said shut-off valve by pneumatic means; the electric currents needed to control electromagnetically actuated valves have been found sufficient to substantially distort measuring results.

If the shut-off valve is controlled pneumatically, it will be advisable to provide, for the purpose of pneumatically controlling the shut-off valve, an electromagnetically controlled valve connected to the source of gas pressure. Said electromagnetically controlled valve will be innocuous unless directly in contact with the reference pressure system, or the first system.

So as to permit the integrity of the membrane filter and the tightness of the first system to be pretested, it will be appropriate to provide a second pressure measuring device connected with the space of the inlet side of the membrane filter.

Another, independent solution of the problem to be solved is seen in the fact that, at the beginning of any measurement, a closed reference pressure system is brought up to the testing gas pressure and that, subsequently, any gas quantities flowing from the reference pressure system to said first system are measured per unit of time.

Since the gas mass per unit of time obtained in this instance is precisely equal to the gas mass passing, per unit of time, through the membrane filter to be tested, the value measured directly indicates the rate of diffusion through said membrane filter; in its turn, this value provides a direct indication as to whether said membrane filter can be used, or not, for its intended purpose. The manufacturers of membrane filters quote maximum values for rate of diffusion. If any rate measured is greater than said maximum value quoted by the manufacturers, said membrane filter is useless. If, on the other hand, the value measured is lower than said level, the membrane filter is unrestrictedly suitable.

According to the invention, a preferential embodiment of the device permitting the method to be performed consists in connecting, via a line and a pressure control valve, the first system on the inlet side of the membrane filter with a source of gas pressure, and by providing a reference pressure system connected via a gas flow measuring device with said first system.

So as to provide for a state of equilibrium whenever the first system and said reference pressure system are brought up to the testing gas pressure, it may be appropriate to connect the reference pressure system with the first system via another line that can be closed immediately prior to the start of any measurement. In this case, it will be possible, when bringing up the reference pressure system to the testing gas pressure, for the gas to flow immediately from the first system into the reference pressure system, there being no need to have it run through the gas flow measuring device.

In a laboratory environment, the rate of any pressure decline measured within a certain filter housing for a certain filter cartridge at a definite testing pressure may be used as a measure of test filter integrity. With testing methods as performed under normal conditions, additional and unavoidable feed lines at the filter housing will increase inlet side volumes; therefore, laboratory values for maximum admissible rates of pressure decline may, at best, be considered standard values. Knowledge about actual rates of diffusion as expressed in units of volume or mass is, thus, not only desirable but indispensable if integrity is to be tested reliably under the diffusion method of testing.

Now, another independent solution of the problem to be solved is deemed to consist in a method permitting the determination of gas diffusion rates through membrane filters in verifying the permeability of membrane filters from their inlet side by first subjecting a wetted membrane filter, on its inlet side, in a first closed system to a first testing gas pressure and measuring the pressure differential per unit of time, characterized in that the first system is subsequently brought up to a second testing gas pressure, in that the overall pressure differential of the first system is determined during a predetermined span of measuring time, and in that, in addition to the pressure gradient caused by gas permeating through the membrane filter, an additional pressure gradient is caused to occur within the first system by bleeding a predetermined quantity of gas from said first system.

In accordance with another preferred embodiment, the method is performed as described above except that, during the measuring time, a predetermined pressure variation of the first system is caused by bleeding off a fixed quantity of gas from the first system.

With both predetermined methods, preferred procedure consists in having the first and second testing gas pressures equal, which considerably simplifies the procedure.

A device permitting the method to be performed is characterized in that the space on the inlet side of the membrane filter is connected, via the line and pressure control valve, with a source of gas pressure, in that a first pressure measuring device is provided within the bypass line of the line between pressure control valve and the space on the inlet side, in that a shut-off valve is provided within the bypass line for the purpose of forming, within the shut-off valve and the pressure measuring device, a reference pressure system, capable of being closed, and in that, together with the space on the inlet side of the membrane filter, a gas draining valve and a gas flow measuring device downstream from said gas draining valve are provided.

Below the invention will be exemplified by preferential embodiments shown in the drawings.

DESCRIPTION OF THE DRAWINGS

FIG. 1 shows a prior art arrangement permitting both initial tesing of membrane filter permeability and subsequent filtration. Within housing 10, there is a rod-shaped membrane filter 11 (membrane filter cartridge). The exterior of said cartridge constitutes the inlet side of the membrane filter and is surrounded by space 12 through which the medium to be filtered, for instance a liquid, is introduced. Interior 13 of the cartridge constitutes the outlet side of membrane filter 11. Within said interior, the filtered medium collects and is drained through bottom end 14 of said cartridge, via line 15 and drain valve 16 within said line. Moreover, pressure measuring device $P_2$ is located within line 15, which device, if connected to pressure measuring device $P_1$ located on the inlet side of said membrane filter and connected with space 12 permits the measurement of the pressure differential prevailing between inlet and outlet sides of membrane filter 11. Furthermore, line 15 comprises valve 17 located within drain sleeve 18. Said sleeve may be connected to hose 19 the free end of which may be introduced into an upended graduated cylinder, 20, located within beaker, 21, filled with liquid.

Figure 1:
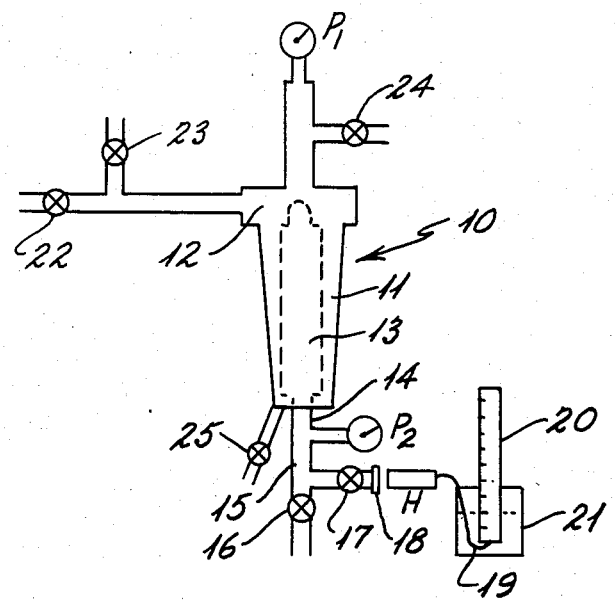
FIG. 1 is a schematic representation of a prior art testing method.

On the inlet side of membrane filter 11, there is inlet valve 22, connected with space 12 which permits the introduction of the medium to be filtered. Another valve, 23, is connected with space 12; through said valve 23, a pressurized gas may be introduced, which gas will permit space 12 to be brought up to a predetermined pressure for the purpose of performing integrity testing as well as filtration. Finally, space 12 comprises another valve, 24, for venting space 12 to atmospheric pressure.

With the so-called gas diffusion testing method, membrane filter 11 is impregnated first; thereupon, space 12, i.e., the inlet side of membrane filter 11, is brought up to a predetermined level of pressure by introducing a gas, e.g. nitrogen, subject to a predetermined level of pressure. Next, the pressure differential across the membrane filter and the quantity of gas having passed, per unit of time, through membrane filter 11 and now collected within graduated cylinder 20, are determined by reading off pressure measuring devices $P_1$ and $P_2$. This measurement permits some conclusions as to the permeability of the membrane filter. Finally, by continuously increasing the pressure acting upon space 12 on the inlet side, the so-called visual bubble point will be determined, which point is reached whenever the velocity of gas bubble production increases significantly at the outlet side, i.e., at the end of hose 19. If the measurements so performed indicate that membrane filter 11 is acceptably permeable, valves 17, 23 and 24 are closed and filtration proper can start.

Figure 2:
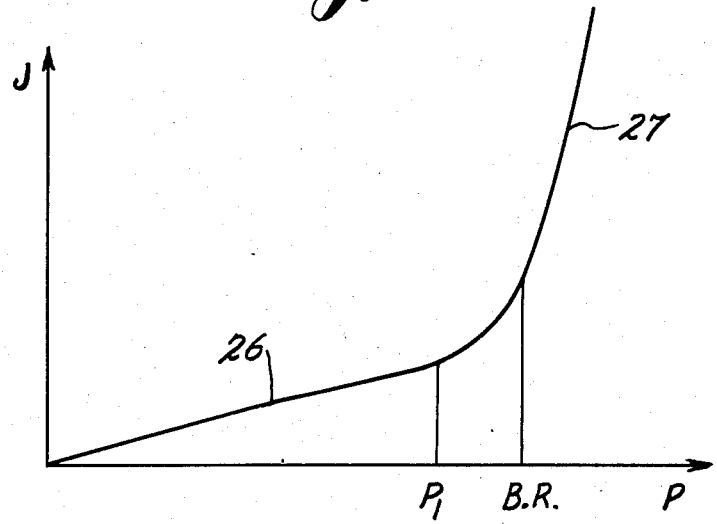
FIG. 2 is a diagram explaining the term "bubble point."

For improved understanding of the term "visual bubble point," reference is made to FIG. 2, where test gas pressure p, as applied to the inlet side of the membrane filter to be tested, is plotted on the abscissa while rate of gas flow J, i.e., the quantity of gas per unit of time diffusing or flowing through the membrane filter at pressure p is plotted on the ordinate. At lower pressures, J and p are proportional to each other. In area 26, gas moves through the membrane filter only by diffusion. Whenever pressure p increases beyond point $p_1$, there will be a deviation from the proportional behavior described above; if pressure p is increased even more, the rate of gas flow permeating the membrane filter, i.e., quantity J, will increase substantially. In area 27, the major part of gas flow J is due, in addition to a certain part applicable to diffusion, to ducts having formed through the membrane filter. Thus, the visual bubble point, as determined in a purely subjective manner according to the amount of the gas flow passing through the membrane filter, is located somewhere within the transitional range between areas 26 and 27; however, with reference to point $p_1$ (the true bubble point of the membrane), it will be displaced towards higher pressure values: in FIG. 2, the visual bubble point is marked by the abbreviation B.P.

Now, this invention tries to find a sensitive method of measuring pressure $p_1$ in FIG. 2 without having to perform any measurement on the outlet side of any membrane filter as represented by cartridge 11 in FIG. 1. With a view towards finding a suiable testing method, the following matters were considered, among others, and finally led to the desired object of a suitable testing method:

Hereinafter, the following designation shall mean:
$p_{test}$ = testing pressure
$V_{up}$ = closed testing volume within the filter housing, on the inlet side of the membrane filter
$V_0$ = volume within the filter housing, on the inlet side of the membrane filter, as normalized to atmospheric pressure
$p_{atm}$ = atmospheric pressure
$V_D$ = volume diffused over time t
$p_t$ = pressure prevailing on the inlet side of the membrane filter subsequent to time t Assuming that temperatures will remain constant during any one measurement, the following equations can be set up:

$$p_t = \frac{(V_0 - V_D) \times p_{atm}}{V_{up}} \quad (1)$$

$$p_t = \frac{V_0 \times p_{atm}}{V_{up}} - \frac{p_{atm} \times V_D}{V_{up}} \quad (2)$$

If equation (3)

$$V_0 = \frac{p_{test} \times V_{up}}{p_{atm}} \quad (3)$$

as applicable to the initial state at the beginning of a measurement, is substituted into equation (2), the following is obtained:

$$p_t = p_{test} - \frac{p_{atm}}{V_{up}} \times V_D \quad (4)$$

By further substituted $$\Delta p = p_{test} - p_t \quad (5)$$

into equation (4) the following is obtained:

$$\Delta p = \frac{p_{atm}}{V_{up}} \times V_D \quad (6)$$

This means that the pressure decline for initial testing pressures will be proportional to the volume diffused corresponding to the region of diffused flow, 26 in FIG. 2, always assuming that atmospheric pressure will remain constant during any individual measurement; this will normally be true since variations may be expected not to exceed ±3%. Moreover, the above result means that any pressure decline will be inversely proportional to the volume existing on the inlet side of the membrane filter within the filter housing, i.e., the sensitivity of any measurement so performed will increaase as the volume of the filter housing on the inlet side of the membrane filter decreases. More particularly, equation (6) shows that pressure decline $\Delta p$ is directly proportional to gas diffusion volumes so that there is a linear relationship between pressure decline and said volume which, in its turn, is a linear function of time (for at least 15 minutes). Whenever volume $V_{up}$ is known, the pressure variation corresponding to any given volume of gas diffusion can be calculated directly.

If maximum pore size for a membrane filter is to be computed precisely, it is important to determine, in accordance with FIG. 2, that pressure p at which its purely diffusion-type flow becomes a combination of diffusion and ducting through the membrane filter. In FIG. 2, by way of example, this occurs at point $p_1$. Whenever said pressure has been determined, it will be possible to determine—even though no details are to be given here—maximum pore size for the membrane filter as a function of thickness, surface, and certain structural assumptions. Manufacturers of membrane filters available for sale, quote pressures at which pressure diffusion-type flow changes into a combination of diffusion and duct-type flow. This manufacturer's estimate provides a basis for checking, prior to using the filter, whether the integrity of the filter is unimpaired and whether pore size is in accordance with requirements. If measurements are obtained which are lower than the pressures quoted by the manufacturer, then the filter is probably damaged.

Figure 3:
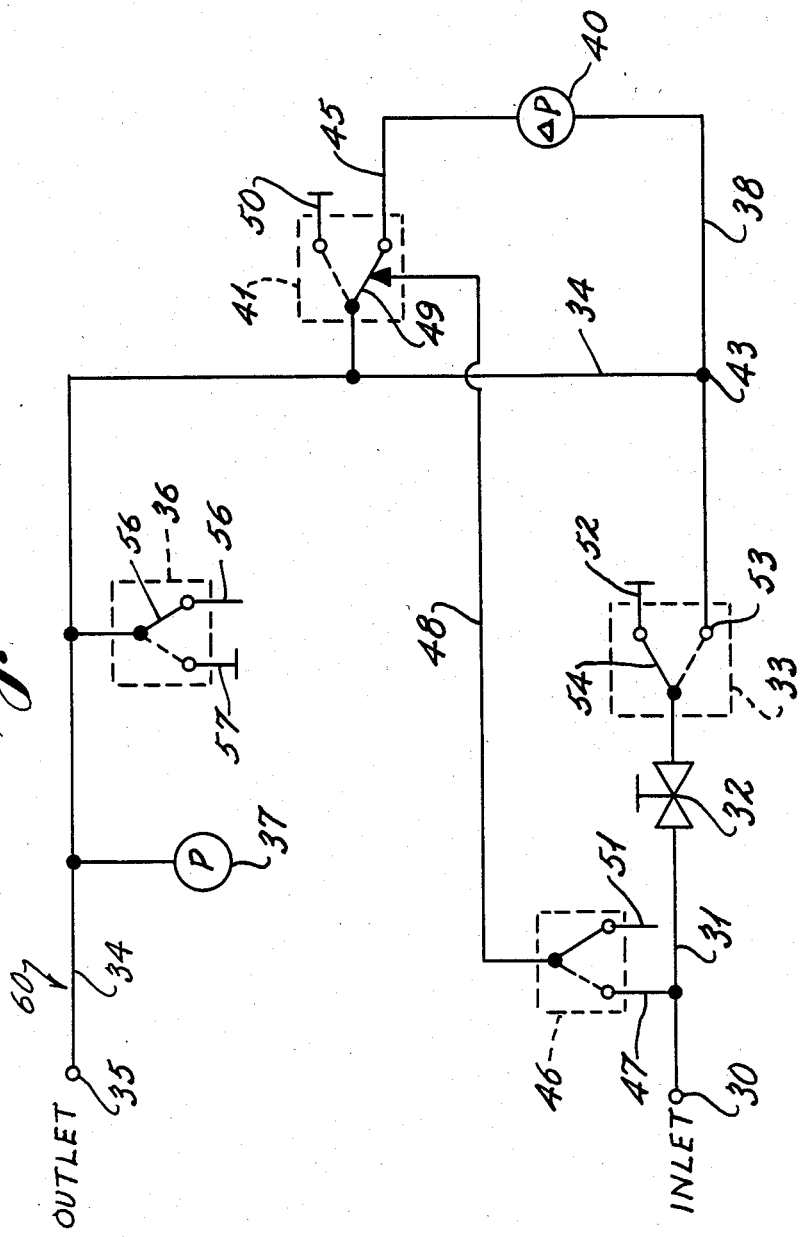
FIG. 3 is a schematic representation of an embodiment of the testing device of the invention.

Below, the preferential method of determining pressure $p_1$ according to FIG. 2 is to be explained on the basis of a preferential embodiment of a measuring device as shown in FIG. 3. At point 30, line 31 may be connected with a source of gas pressure, not shown, e.g. a reservoir containing nitrogen at a pressure of 7 bars. Via needle valve 32 and a first electromagnetic valve, 33, line 31 is connected with line 34 which functions as a common manifold for the connecting lines seen in FIG. 3. At point 35, line or manifold 34 may be connected, e.g. with valve 24 of FIG. 1, for link-up to system 10. Line 34 is connected with venting valve 36. Moreover, line 34 is connected with a first pressure measuring device, 37, permitting the determination of absolute pressure p prevailing within line 34. In bypass line 38 of line 34, a second pressure measuring device, 40, and pneumatically controllable valve 41 are arranged in series. At points 43 and 44, bypass line 38 ties into line 34. The second pressure measuring device, 40, is used to measure the pressure differential between the pressure prevailing in line 34 and within that section of line 38 located between the second pressure measuring device, 40, and pneumatically controllable valve 41. As will be explained in detail below, this section of said line forms reference pressure system 45.

Another electromagnetically controllable valve, 46, is provided to permit controlling pneumatically controllable valve 41; via connection 47, valve 46 ties into line 31 while being connected, moreover, with line 48. Line 48 leads to change-over 49 of pneumatically controllable valve 41; moreover, there is an arrangement, not shown in detail, such that, whenever the pressure prevailing in line 48 is above atmospheric pressure, change-over switch 49 will move from its position shown in FIG. 3, which position connects lines 38 and 34, into the position shown in broken lines, which position interrupts the connection line 34 and reference pressure system 45, and in which both reference pressure system 45 and the connection linking line 34 to the pneumatically controllable valve 41 will be closed. The end of the line corresponding to the broken-line position of valve 41 is represented by cut-off line section 50.

In its deactivated position, as shown, electromagnetically controllable valve 46 establishes a connection between line 48 and line 51 which line 51 opens out into the atmosphere. In its activated position, shown as a broken line, valve 46 connects lines 31 and 48 via connection 47.

It is position shown in FIG. 3, first electromagnetic valve 33 connects line 31 and closed end 52 of valve 33 via pressure reducing valve 32. In said valve position, line 34 is likewise closed at point 53. In the activated state of the first electromagnetic valve, 33, change-over switch 54 will be in the position shown in broken lines. In this position, needle valve 32 is directly connected with line 34.

Venting valve 36 is likewise shown in the position with its solenoid deactivated. In said position, line 34 is connected, via change-over switch 55, with outlet 56, which outlet is open to atmospheric air. Upon activation of venting valve 36, change-over switch 55 is thrown into the position shown in broken lines, in which position line 34 is connected with closed end 57.

In FIG. 3, all of valves 33, 36, 41 and 46 are shown deactivated.

In order to test a membrane filter already built in, e.g. into housing 10 according to FIG. 1, the test measuring device globally designated 60 is placed next to valve 24 at point 35 and tightly connected with said valve. Thereupon, valve 36 will be activated, causing it to close. Next, valve 33 will be activated so that needle valve 32 and line 34 are connected. Next, the pressure within line 34 is adjusted to a predetermined testing gas pressure. Said testing gas pressure will be measured by way of the first pressure measuring device, 37. Whenever the pressure erroneously increases beyond the maximum admissible pressure of approx. 7 bars, pressure measuring device 37 will automatically transmit a signal to venting valve 36, causing it to be deactivated.

Upon such deactivation, line 34 will open out to the atmosphere so that any excess pressure can be reduced and even further gas supplies cannot cause excess pressure to build up within the system. Rather, all the gas is vented directly to the atmosphere.

As soon as the predetermined testing gas pressure has been reached, valve 33 will be deactivated so that line 34 is closed at point 53. Thus, deactivation of valve 33 forms a closed system existing within line 34 and space 12 (of FIG. 1) on the inlet side of membrane filter 11. From this moment in time, the pressure decline within said closed system is measured as a function of time. A rapid pressure decline may mean either that the system itself has a leak or that the membrane filter is defective. This measurement may be deemed a preliminary one intended to guarantee that there are no major leaks. During this measurement, there is no need for pressure measuring device 40. Since the pressures prevailing on either side of said measuring device are equal, it may not be damaged. As soon as the system has been found to be tight, the first test on membrane filter permeability can be run. To do so, valve 33 as activated and line 34 and the system connected therewith are brought up to a first testing gas pressure, if possible to a value below $p_1$ according to FIG. 2. Thereupon, valve 33 is deactivated. Since reference pressure system 45 and line 34 are connected via valve 41, the testing gas pressure prevailing in reference system 45 at that moment in time will be at the same level as the one within line 34. Next, valve 46 is activated so that line 48 is separated from the atmosphere and is connected with line 31, which is subject to approx. 7 bars of increased pressure. This will cause change-over switch 49 of pneumatically controllable valve 41 to move over into the position shown by broken lines in FIG. 3, which isolates reference pressure system 45. As from this moment in time, pressure measuring device 40 will be used to measure the pressure decline occurring between the pressure prevailing within line 34 and the one in reference pressure system 45. According to equation (6), said pressure differential $\Delta p$ is proportional to gas diffusion volume $V_D$ permeating through the membrane filter. The value of $\Delta p$ per t, i.e. the pressure differential per unit of time, is directly proportional to the value of J in accordance with FIG. 2. In order to be sure a constant value has been obtained, the measurement is continued over four to five minutes. Values obtained via pressure measuring device 40 may be recorded by means of a recorder, or stored in a magnetic memory. At the end of such measurement, valve 46 is deactivated once more, which likewise deactivates valve 41 by connecting line 34 with reference pressure system 45 so that the pressures prevailing on the two sides of pressure measuring device 40 are equalized. Thereupon, venting valve 36 may be actuated; however, this is unnecessary if, by way of example, the system is to be brought up, for the next measurement, to a pressure higher than the one for the first measurement. Thereupon, a second measurement can be made according to the same procedure as the one described above, except that the system consisting of line 34 and space 12 is now brought up to a pressure p greater than the value of the first measurement. Other measurements may follow, provided their initial p value is greater than the preceding one. As long as the measuring system is operated within the range characterized by diffusion and designated 26 in FIG. 2, the values obtained ought to result in a linear function, i.e. they have to form a straight line when plotted as in FIG. 2. Whenever the value for J obtained for the most recent value of p in a series of increasing pressures deviates from said straight line, such deviation indicates that during the previous measurement, the point was passed which separates the region where the gas flows through the membrane only by diffusion from the region where gas flows through the membrane by diffusion and ducting. The value of p previously obtained may then be used either to directly compute the size of membrane filter pores or to check, based on the data quoted by the manufacturers, whether the membrane filter being tested meets pore size requirements.

Subsequent to this measurement, venting valve 36 can be deactivated so that the entire system will once more be under atmospheric pressure. Another advantage of the system shown in FIG. 3 consists in the fact that no power failure will damage the system. In such event, no overpressure can build up within the system since said venting valve will be open to the atmosphere.

Pressure measuring devices 37 and 40 may be conventional instruments, if possible providing an electrical output signal which may be used to record the pressure obtained directly by way of a recorder, to drive a digital or analog display, or which can be directly transmitted to a suitable computer.

Another substantial advantage of the system shown in FIG. 3 consists in the fact that reference pressure system 45, line 34, and space 12 may directly be brought up to the same testing gas pressure at a single stroke, i.e., by activating vave 33. On the one hand, this expedites measuring procedures while, on the other hand, it is guaranteed that testing gas pressures both in the measuring system and in the reference pressure system were at the same level at the beginning of any measurement. The preceding procedure notwithstanding, the method could be applied so as to bring the reference pressure system up to the testing gas pressure irrespective of line 34. In this case, it would not be necessary to separate the reference pressure system from the source of gas pressure if it can be guaranteed that the source of gas pressure will reliably remain at testing gas pressure during the entire measurement. However, it will be preferable to isolate the reference pressure system whenever the testing gas pressure has been reached.

The essential advantage of the method described above consists in the fact that measurements can be made on the inlet side of the membrane filters so that the measuring procedure per se will not contaminate a sterile filter. Moreover, there is the possibility of determining, to an extremely high degree of precision, the pressure at which the transition from purely gas diffusion flow to a combination of diffusion and duct-type flow through the membrane filter occurs. This permits the maximum size of membrane filter pores to be determined in an extremely precise manner.

By another embodiment of the invention, ways and means were sought of directly determining, if at all possible, the value for the rate of diffusion through cartridge 11, since this value may be compared directly to the one provided by the manufacturer of such membrane filter and will provide a simple means of determining whether said filter is defective or in working order. Thus, the aim is to measure quantity J indicating the volume of gas having diffused through the membrane filter per unit of time. Measuring quantity J is difficult because no measurements may be made, for sterility's sake, on the outlet side of the membrane filter. So as to permit quantity J to be measured, the following preferential embodiment of a measuring device is proposed in accordance with the invention.

Figure 4:
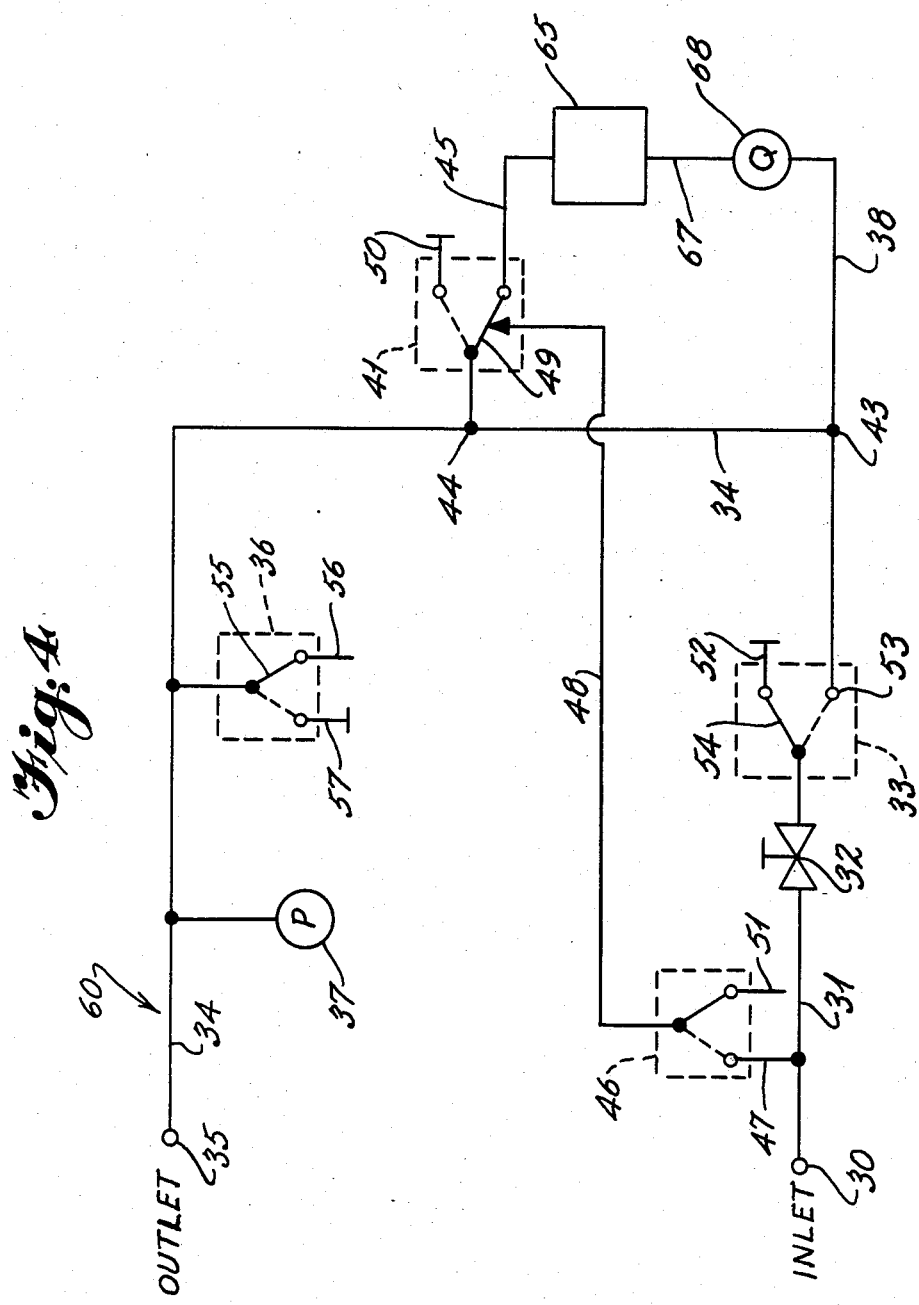
FIG. 4 is a schematic representation of a second embodiment of the testing device of the invention.

FIG. 4 shows a measurng device similar to the one used in FIG. 3. Identical references mean functionally identical components, so there is no need to discuss them in detail. Said measuring arrangement is distinguished from the arrangement shown in FIG. 3 in that pressure measuring device 40 in bypass 38 of line 34, which functions as a common manifold for the connecting lines seen in FIG. 4, has been replaced by gas flow metering device 68 connected in series to reference pressure system 65 in the form of a pressure vessel and inserted between line 38 and pneumatically controllable valve 41. The function of gas flow metering device 68 is to measure the gas flowing from reference pressure system 65 into line or manifold 34.

In order to test a membrane filter already built in, e.g. into housing 10 according to FIG. 1, the test measuring device globally designated 60 is placed next to valve 24 at point 35 and tightly connected with said valve. Thereupon, valve 36 will be activated, causing it to close. Next, valve 33 will be activated so that needle valve 32 and line 34 are connected. Next, the pressure within line 34 is adjusted to a predetermined testing gas pressure. Said testing gas pressure will be measured by way of the first pressure measuring device, 37. Whenever the pressure erroneously increases beyond the maximum admissible pressure of approx. 7 bars, pressure measuring device 37 will automatically transmit a signal to venting valve 36, causing it to be deactivated. Upon such deactivation, line 34 will open out to the atmosphere so that any excess pressure can be reduced and even further gas supplies cannot cause excess pressure to build up within the system. Rather, all the gas is vented directly to the atmosphere.

As soon as the predetermined testing gas pressure has been reached, valve 33 will be deactivated so that line 34 is closed at point 53. Thus, deactivation of valve 33 forms a closed system existing within line 34 and space 12 of FIG. 1 on the inlet side of membrane filter 11. From this moment in time, the pressure decline within said closed system is measured as a function of time. A rapid pressure decline may mean either that the system itself has a leak or that the membrane filter is defective. This measurement may be deemed a preliminary one intended to guarantee that there is no need for flow metering device 68. As soon as the system has been found to be tight, the first test on membrane filter permeability can be run. To do so, valve 33 is activated and line 34 and the system connected therewith are brought up to a first testing gas pressure amounting to approx. 80% of the so-called bubble-point pressure. Thereupon, valve 33 is deactivated. Since reference pressure system 65 and line 34 are connected via valve 41, the testing gas pressure prevailing in reference system 65 at that moment in time will be at the same level as the one within line 34. Next, valve 46 is activated so that line 48 is separated from the atmosphere and is connected with line 31, which is subject to approx. 7 bars of increased pressure. This will cause change-over switch 49 of pneumatically controllable valve 41 to move over into the position shown by broken lines in FIG. 4, which isolates reference pressure system 65. From this moment in time, the gas flow is measured through flow metering device 68 of line 38. In order to be sure a constant value has been obtained, the measurement is continued over 4 to 5 minutes. Values obtained via flow metering device 68 may be recorded by means of a recorder, or stored in a magnetic memory. At the end of such measurement, valve 46 is deactivated once more, which likewise deactivates valve 41 by connecting line 34 with reference pressure system 65 so that the pressure prevailing on the two sides of flow metering device 68 are equalized. Thereupon, venting valve 36 may be actuated; however, this is unnecessary if, by way of example, the system is to be brought up, for the next measurement, to a pressure higher than the one for the first measurement. Thereupon, a second measurement can be made according to the same procedure as the one described above, except that the system consisting of line 34 and space 12 is now brought up to a pressure p greater than to the value of the first measurement. Other measurements may follow, provided their initial p value is greater than the preceding one. As long as the measuring system is operated within the range characterized by diffusion, designated 26 in FIG. 2, values obtained ought to result in a linear function, i.e., the quality of volumetric gas flow measured per unit of time ought to be directly proportional to the testing gas pressure.

Subsequent to this measurement, venting valve 36 can be deactivated so that the entire system will once more be under atmospheric pressure. Another advantage of the system shown in FIG. 4 consists in the fact that no power failure will damage the system. In such event, no over-pressure can build up within the system since said venting valve will be open to the atmosphere.

Another substantial advantage of the system shown in FIG. 4 consists in the fact that the reference pressure system 65, line 34 and space 12 may directly be brought up to the same testing gas pressure at a single stroke, i.e., by activating valve 33 via change-over valve 41. On the one hand, this expedites the measuring procedure while, on the other hand, it guarantees that testing gas pressures both in the measuring system and in the reference pressure system were at the same level at the beginning of any measurement. The preceding procedure notwithstanding, the method could be applied so as to bring the reference pressure system up to the testing gas pressure irrespective of line 34. In this case, it would not be necessary to separate the reference pressure system from the source of gas pressure if it can be guaranteed that the source of gas pressure will reliably remain at the testing gas pressure during the entire measurement. However, it will be preferable to isolate the reference pressure system whenever the testing gas pressure has been reached. Of course, it is not really necessary to connect reference pressure system 65, via line 45 and valve 41, with line 34. Properly speaking, it would be enough to link reference pressure system 65 via line 38 and flow metering device 68. However, since the flow metering device might cause certain bottlenecks, particularly as regards reverse flows, which bottlenecks might increase the time needed for the reference pressure system to be brought up to testing gas pressures, the system shown in FIG. 4 is preferred.

The manufacturers of membrane filters invariably quote a value for maximum rate of gas diffusion through the membrane filter, e.g. 10 ml per minute at a testing pressure of $p_{test}=2.5$ bars, in order to provide membrane filter users with a reference point for testing the filter, prior to using it, so as to tell whether it is subject to any defects, or may be used unrestrictedly. Anyone wanting to test, prior to filtration, the integrity and suitability for its intended use of any such membrane filter is faced with the problem of performing this test exclusively on the inlet side of the membrane filter and to determine, if at all possible, the rate of gas diffusion through the membrane filter in order to obtain a value which can be compared directly with manufacturer's data as to maximum speed of gas diffusion.

Below, another method of verifying said values is described. From equation (6) it can be seen that pressure variation over time is proportional to rate (J) of gas diffusion. Hitherto, it has been impossible to obtain an absolute value for said rate of gas diffusion since the formula set forth above shows that the volume ($V_{up}$) present on the inlet side of the membrane filter has to be taken into account in this measurement, and since it had hitherto been impossible to determine said value without complicated apparatus.

Figure 6:
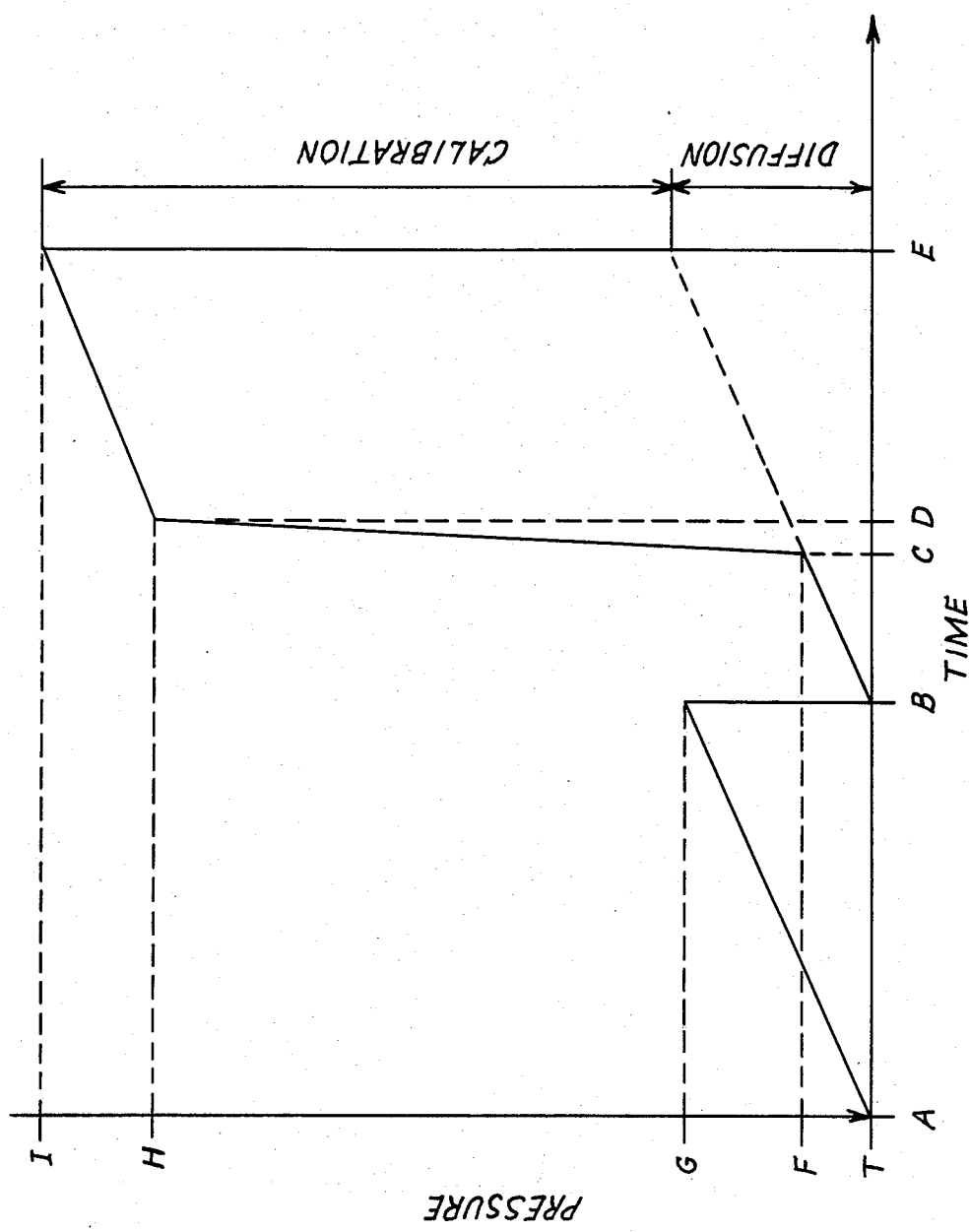
FIG. 6 is a diagram showing loss of pressure as a function of time during the performance of the testing method of the invention.

It is now possible to directly determine the rate of gas diffusion according to the following method, which is to be explained diagrammatically in FIG. 6. In said diagram, pressure is plotted descendingly along the ordinate. Time is plotted along the abscissa. At moment in time A, the system is brought up to testing gas pressure T on the inlet side of the membrane filter. During period ($\overline{AB}$), a pressure decline amounting to ($\overline{TG}$) occurs. Since said pressure decline occurs as a linear function of time, the rate of pressure decline (p') may be determined by dividing $\overline{TG}$ by $\overline{AB}$. Subsequent to determining rate p' of pressure decline, testing pressure is brought up to T at moment in time B. Subsequent to an arbitrary lapse of time, $\overline{BC}$, during which another pressure loss, $\overline{TF}$, occurs, a known volume V of gas will be drained from the system on the inlet side of the membrane filter over period of time $\overline{CD}$, of arbitrary duration. In addition to the loss of pressure due to diffusion, there will be another pressure decline, $\overline{FH}$. At an arbitrary moment in time, E, the measuring procedure is stopped after determination of $\overline{TI}$, the amount of pressure lost over period $\overline{BE}$.

If rate p' of pressure decline over period AB, loss TI of pressure and calibration time BE are known, the pressure decline per unit of volume can be determined as follows:

$$\frac{\overline{FH}}{V} = \frac{\overline{TI} - p' \times \overline{BE}}{V} \qquad (7)$$

$$J = \frac{V_D}{t} = \frac{\frac{\Delta p}{\Delta t}}{\frac{\Delta p}{\Delta V}} = \frac{p'}{\frac{\overline{FH}}{V}} \qquad (8)$$

By substituting the value obtained in equation (7) into equation (8), the following is obtained:

$$J = \frac{p' \times V}{(\overline{TI} - p' \times \overline{BE})} \qquad (9)$$

If standard conditions, i.e., a temperature of 20° C. and a pressure of 1,013 mbar are to be applied to the above equation, factors $p_{atm}$ and T as well as a constant amounting to 3.457 have to be introduced into equation (9), the applicable unit being pressure divided by temperature;

T corresponds to the absolute temperature in degrees Kelvin (K.), and $p_{atm}$ corresponds to the air pressure expressed in mbar.

As regards speed of gas diffusion, the following expression results $$J = \frac{p' \times V \times P_{atm}}{(\overline{TI} - p' \times \overline{BE}) \times T \times 3.457} \left( \frac{\text{units of volume}}{\text{unit of time}} \right) \quad (10)$$

Figure 5:
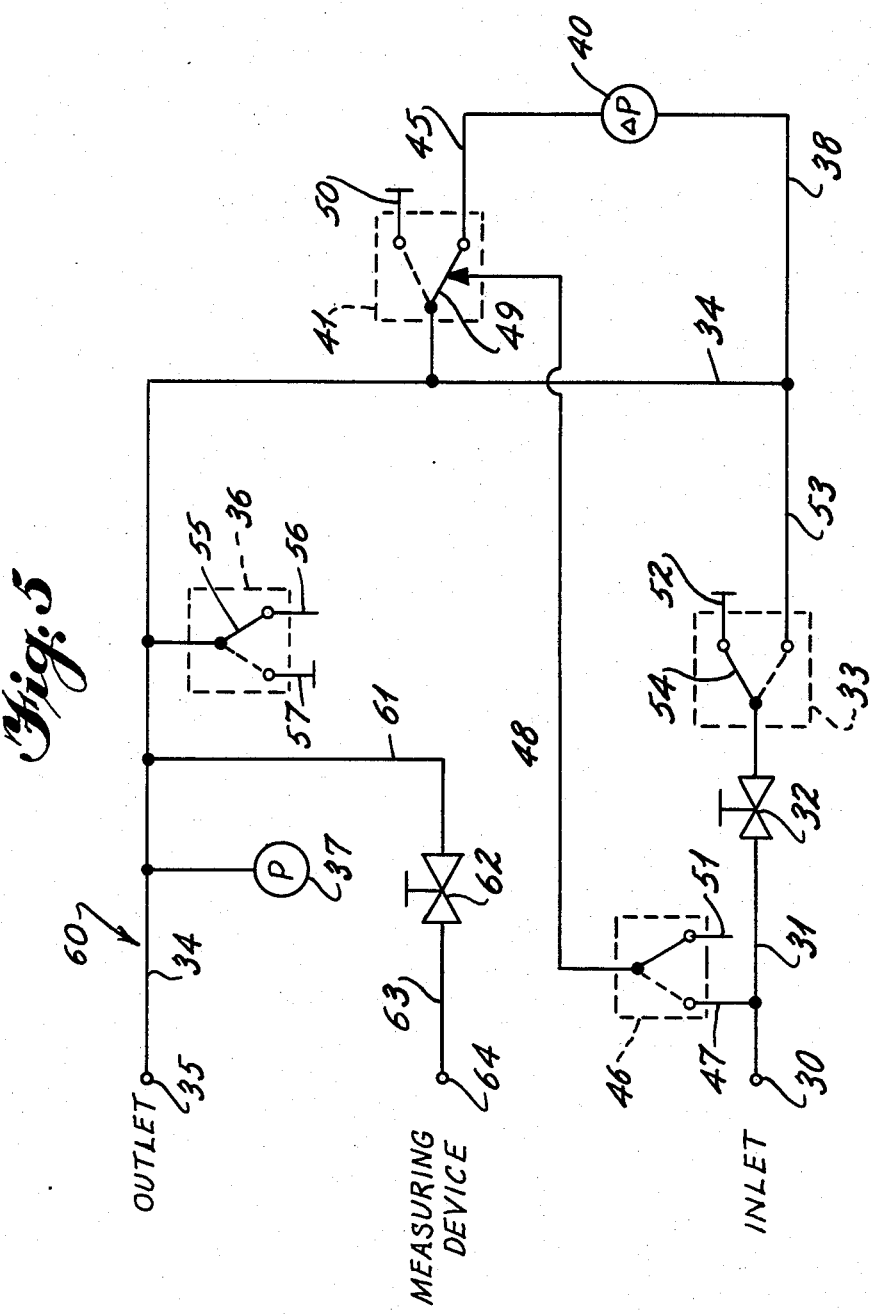
FIG. 5 is a schematic representation of a third embodiment of the testing device of the invention.

The testing method is applied by means of a system as described in FIGS. 1 and 5. Measuring procedure is shown diagrammatically in FIG. 6.

In order to determine the rate of gas diffusion and to test the integrity of a membrane filter already built in, e.g. into housing 10 according to FIG. 1, the test measuring device globally designated 60 is placed next to valve 24 at point 35 and tightly connected with said valve. At this moment in time, control valve 62 is closed. Thereupon, valve 36 will be activated, causing it to close. Next, valve 33 will be activated so that needle valve 32 and line 34, which functions as a common manifold for the connecting lines seen in FIG. 5, are connected. Next, the pressure within line 34 is adjusted to a predetermined testing gas pressure. Said testing gas pressure will be measured by way of the first pressure measuring device, 37. Whenever the pressure erroneously increases beyond the maximum admissible pressure of approx. 7 bars, pressure measuring device 37 will automatically transmit a signal to venting valve 36, causing it to be deactivated. Upon such deactivation, line or manifold 34 will open out to the atmosphere so that any excess pressure can be reduced and even further gas supplies cannot cause excess pressure to build up within the system. Rather, all the gas is vented directly to the atmosphere.

As soon as the predetermined testing gas pressure has been reached, valve 33 will be deactivated so that line 34 is closed at point 53. Thus, deactivation of valve 33 forms a closed system existing within line 34 and space 12 (of FIG. 1) on the inlet side of membrane filter 11. From this moment in time, the pressure decline within said closed system is measured as a function of time. A rapid pressure decline may mean either that the system itself has a leak or that the membrane filter is defective. This measurement may be deemed a preliminary one intended to guarantee that there are no major leaks. During this measurement, there is no need for pressure measuring device 40. Since the pressure prevailing on either side of said measuring device are equal, it may not be damaged. As soon as the system has been found to be tight, the first test on membrane filter permeability can be run. To do so, valve 33 is activated and line 34 and the system connected therewith are brought up to a first testing gas pressure. Thereupon, valve 33 is deactivated. Since reference pressure system 45 and line 34 are connected via valve 41, the testing gas pressure prevailing in reference system 45 at that moment in time will be at the same level as the one within line 34. Next, valve 46 is activated so that line 48 is separated from the atmosphere and is connected with line 31, which is subject to approx. 7 bars of increased pressure. This will cause change-over switch 49 of pneumatically controllable valve 41 to move over into the position shown by broken lines in FIG. 5, which isolates reference pressure system 45. From this moment in time, pressure measuring device 40 will be used to measure the pressure decline occurring between the pressure prevailing within line 34 and the one in reference pressure system 45. In the process, $\Delta p$ per t, i.e., the pressure differential per unit of time, or the pressure differential $\overline{TG}$ per $\overline{AB}$, is measured. In order to obtain a high enough degree of precision, the measurement is continued over 4 to 5 minutes. Values obtained via pressure measuring device 40 may be recorded by means of a recorder, or stored in a magnetic memory. At the end of such measurement, valve 46 is deactivated once more, which likewise deactivates valve 41 by connecting line 34 with reference pressure system 45 so that the pressure prevailing on the two sides of pressure measuring device 40 are equalized. Thereupon, venting valve 36 may be actuated; however, this may be unnecessary since the system would be brought up again, e.g. if measurements go on, to some testing gas pressure. By means of line 34 and reference pressure system 45, the system is subsequently brought up to its test pressure, preferably the initial one; according to the diagram in FIG. 6 this ought to be achieved by moment in time B. Subsequent to the end of any pressure decline measurement, some period of time may obviously lapse until the system is back to testing gas pressure T. Time, corresponding to $\overline{BE}$, will begin running and will be measured as soon as the measurement is initiated. After an arbitrary period of time, e.g. $\overline{BC}$, subsequent to the initiation of said second measurement, control valve 62 is opened at moment in time C, and, simultaneously, a predetermined volume of gas, V, measured by means of a suitable measuring device, will be drained from line 34. Thereupon, control valve 62 is closed again. By draining the volume of gas from line 34, an additional decline of system pressure, of quantity $\overline{FH}$, is caused to occur. Said decline will be added to the one amounting to TF to which the system is subject due to gas diffusion through the membrane filter at moment in time C. At moment in time D, i.e., when control valve 62 is closed, an overall pressure of H prevails within the system. During period of time $\overline{DE}$, said pressure will be reduced by pressure differential $\overline{HI}$. Said reduction is entirely due to the diffusion of gas through the membrane filter. At moment in time E, this second measurement is terminated; period BE and overall pressure decline $\overline{TI}$ can now be determined. Thereupon, the system may be returned, as discussed above, to its initial state, i.e., to atmospheric pressure. Upon determination of the values applicable to the rate of pressure decline p' due to diffusion, to predetermined volume V drained from the system via control valve 62, to period of time BE corresponding to the duration of the second measurement, and to the total decline $\overline{TI}$ in pressure during said second measurement, equation (11) may be used to unequivocally determine the rate of diffusion. Every such quantity may be recorded automatically and transmitted to a suitable data processor for automatic determination of J.

I claim:

1. Method for testing the permeability of membrane filters by submitting, within a first, closed system, the inlet side of a wetted membrane filter to a predetermined testing gas pressure and measuring the pressure gradient over time within said first, closed system, characterized in that a reference pressure system is brought up to the testing gas pressure at the beginning of any measurement and that the pressure gradient is determined by way of the pressure differential between said first, closed system and said reference pressure system.

2. A method for testing the permeability of membrane filters, said method comprising the steps of:
   placing a wetted membrane filter into a housing, said housing having an inlet compartment and an outlet compartment separated by said membrane filter, said housing having a gas manifold attached thereto on the inlet side of said membrane filter, said gas manifold having a source of gas pressure connected thereto by means which allow said source of gas pressure to be either open to or isolated from said gas manifold connected to said inlet side of said membrane filter, when said wetted membrane filter is placed into said housing, said source of gas pressure is isolated from said gas manifold connected to said inlet side of said membrane filter, said gas manifold further having a reference pressure system connected thereto, said reference pressure system comprising a reference pressure source and a differential pressure measuring means, said differential pressure measuring means is connected to said gas manifold connected to said membrane inlet side of said membrane filter and connected to said reference pressure source, said differential pressure measuring means is further connected to a recording means, said reference pressure source is connected to said source of gas pressure by means which allow said reference pressure source to be either open to or isolated from said source of gas pressure, when said wetted membrane filter is placed into said housing, said reference pressure source is isolated from said source of gas pressure;

opening said gas pressure source to said gas manifold connected to said inlet side of said membrane filter;

pressurizing said gas manifold connected to said inlet side of said membrane filter and thereby said inlet side of said membrane filter to a predetermined testing gas pressure by flowing gas from said source of gas pressure into said gas manifold connected to said inlet side of said membrane filter;

isolating said gas pressure source from said gas manifold connected to said inlet side of said membrane filter when said predetermined testing gas pressure is reached;

opening said gas pressure source to said reference pressure source;

pressurizing said reference pressure source to said predetermined testing gas pressure by flowing gas from said source of gas pressure into said reference pressure source;

isolating said gas pressure from said reference pressure source when said predetermined testing gas pressure is reached;

measuring the pressure differential, for a predetermined period of time, between the pressure in said reference pressure source and the pressure in said gas manifold connected to said inlet side of said membrane filter using said differential pressure measuring means; and recording the measurements obtained from said differential pressure measuring means using said recording means.

3. The method of claim 2 wherein:

the steps of opening said gas pressure source to said gas manifold and said reference pressure source occur simultaneously;

the steps of pressurizing said gas manifold and said reference pressure source to said predetermined testing gas pressure occur simultaneously; and the steps of isolating said gas pressure source from said gas manifold and said reference pressure source occur simultaneously.

4. A method for testing the pemeability of membrane filters, said method comprising the steps of:

placing a wetted membrane filter into a housing, said housing having an inlet compartment and an outlet compartment separated by said membrane filter, said housing having a gas manifold attached thereto on the inlet side of said membrane filter, said gas manifold having a source of gas pressure connected thereto by means which allow said surface of gas pressure to be either open to or isolated from said gas manifold connected to said inlet side of said membrane filter, when said wetted membrane filter is placed into said housing, said source of gas pressure is isolated from said gas manifold connected to said inlet side of said membrane filter, said gas manifold further having a reference pressure system connected thereto, said reference pressure system comprising a reference pressure source and a differential pressure measuring means, said differential pressure measuring means is connected to said gas manifold connected to said inlet side of said membrane filter and connected to said reference pressure source, said differential pressure measuring means is further connected to a recording means, said reference pressure source is connected to said gas manifold by means which allow said reference pressure source to be either open to or isolated from said gas manifold, when said wetted membrane filter is placed into said housing, said reference pressure source is open to said gas manifold connected to said inlet side of said membrane filter;

opening said gas pressure source to said gas manifold connected to said inlet side of said membrane filter;

pressurizing said gas manifold connected to said inlet side of said membrane filter, and thereby said inlet side of said membrane filter and said reference pressure source, to a predetermined testing gas pressure by flowing gas from said source of gas pressure into said gas manifold connected to said inlet side of said membrane filter;

isolating said gas pressure source from said gas manifold connected to said inlet side of said membrane filter when said predetermined testing gas pressure is reached;

isolating said reference pressure source from said gas manifold connected to said inlet side of said membrane filter;

measuring the pressure differential, for a predetermined period of time, between the pressure in said reference pressure source and the pressure in said gas manifold connected to said inlet side of said membrane filter using said differential pressure measuring means; and recording the measurements obtained from said differential pressure means using said recording means.

5. The method of claim 4 which comprises the further steps of:

prior to said step of isolating said reference pressure source from said gas manifold connected to said inlet side of said membrane, measuring the drop in pressure in said gas manifold connected to said inlet side of said membrane and in said reference pressure source;

recording the measurements obtained; and stopping the test if said measurements indicate that said membrane filter is leaking or damaged.

6. A method for calibrating a measurement system for testing the permeability of membrane filters, said method comprising the steps of:

placing a wetted membrane filter into a housing, said housing having an inlet compartment and an outlet compartment separated by said membrane filter, said housing having a gas manifold attached thereto on the inlet side of said membrane filter, said gas manifold having a source of gas pressure connected thereto by means which allow said source of gas pressure to be either open to or isolated from said gas manifold connected to said inlet side of said membrane filter, when said wetted membrane filter is placed into said housing, said source of gas pressure is isolated from said gas manifold connected to said inlet side of said membrane filter, said gas manifold further having a reference pressure system connected thereto, said reference pressure system comprising a reference pressure source and a differential pressure measuring means, said differential pressure measuring means is connected to said gas manifold connected to said inlet side of said membrane filter and connected to said reference pressure source, said differential pressure measuring means is further connected to a recording means, said reference pressure source is connected to said gas manifold by means which allow said reference pressure source to be either open to or isolated from said gas manifold, when said wetted membrane filter is placed into said housing, said reference pressure source is open to said gas manifold connected to said inlet side of said membrane filter;

opening said gas pressure source to said gas manifold connected to said inlet side of said membrane filter;

pressurizing said gas manifold connected to said inlet side of said membrane filter and thereby, said inlet side of said membrane filter and said reference pressure source, to a predetermined testing gas pressure by flowing gas from said source of gas pressure into said gas manifold connected to said inlet side of said membrane filter;

isolating said gas pressure source from said gas manifold connected to said inlet side of said membrane filter when said predetermined testing gas pressure is reached;

isolating said reference pressure source from said gas manifold connected to said inlet side of said membrane filter;

measuring the pressure differential, for a predetermined period of time, between the pressure in said reference pressure source and the pressure in said gas manifold connected to said inlet side of said membrane filter using said differential pressure measuring means;

recording the measurements obtained from said differential pressure measuring means using said recording means;

opening said reference pressure source to said gas manifold connected to said inlet side of said membrane filter;

opening said gas pressure source to said gas manifold connected to said inlet side of said membrane filter;

repressurizing said gas manifold connected to said inlet side of said membrane filter, and thereby said inlet side of said membrane filter and said reference pressure source to a second predetermined testing gas pressure, which may be the same as said first predetermined testing gas pressure, by flowing gas from said source of gas pressure into said gas manifold connected to said inlet side of said membrane filter;

isolating said gas pressure source from said gas manifold connected to said inlet side of said membrane filter when said second predetermined testing gas pressure is reached;

isolating said reference pressure source from said gas manifold connected to said inlet side of said membrane filter;

measuring the pressure differential, for a predetermined period of time, between the pressure in said reference pressure source and the pressure in said gas manifold connected to said inlet side of said membrane filter using said differential pressure measuring means;

recording the measurements obtained from said differential pressure measuring means using said recording means;

releasing a predetermined volume of gas from said gas manifold connected to the inlet side of said membrane filter;

measuring the pressure differential, resulting from said release of said predetermined volume of gas between the pressure in said reference pressure source and the pressure in said gas manifold connected to said inlet side of said membrane filter using said differential pressure measuring means;

recording the measurements obtained from said differential pressure measuring means using said recording means;

stopping said release of gas from said gas manifold once said predetermined volume of gas has been released; and calculating the flow rate through said membrane filter.

7. A device for testing the premeability of membrane filters, said device comprising:

a housing, said housing having an inlet compartment and an outlet compartment separated by a wetted membrane filter;

a gas manifold attached to said housing on the inlet side of said membrane filter;

a source of gas pressure connected to said gas manifold by means which allow said source of gas pressure to be either open to or isolated from said gas manifold connected to said inlet side of said membrane filter;

a reference pressure system comprising a reference pressure source and a differential pressure measuring means;

said differential pressure measuring means connected to said reference pressure source and connected to said gas manifold connected to said inlet side of said membrane filter;

said reference pressure source connected to said source of gas pressure by means which allow said reference pressure source to be either open to or isolated from said source of gas pressure; and recording means connected to said differential pressure measuring means.

8. The device of claim 7 wherein said means which allow said reference pressure source to be either open to or isolated from said source of gas pressure is a pneumatically controlled shut-off valve.

9. The device of claim 8 wherein an electromagnetically controlled valve is provided to control said pneumatically controlled shut-off valve.

10. The device of claim 7 wherein a second pressure measuring device is connected to said inlet side of said membrane filter.

11. A device for testing the premeability of membrane filters, said device comprising:

a housing, said housing having an inlet compartment and an outlet compartment separated by a wetted membrane filter;

a gas manifold attached to said housing on the inlet side of said membrane filter;

a source of gas pressure connected to said gas manifold by means which allow said source of gas pressure to be either open to or isolated from said gas manifold connected to said inlet side of said membrane filter;

a reference pressure system comprising a reference pressure source and a differential pressure measuring means;

said differential pressure measuring means connected to said reference pressure source and connected to said gas manifold connected to said inlet side of said membrane filter;

said reference pressure source connected to said gas manifold by means which allow said reference pressure source to be either open to or isolated from said gas manifold; and recording means connected to said differential pressure measuring means.

12. The device of claim 11 wherein said means which allow said reference pressure source to be either open to or isolated from said gas manifold is a pneumatically controlled shut-off valve.

13. The device of claim 12 wherein an electromagnetically controlled valve is provided to control said pneumatically controlled shut-off valve.

14. The device of claim 11 wherein a second pressure measuring device is connected to said inlet side of said membrane filter.

15. The device of claim 11 wherein a gas release control valve is connected to said gas manifold connected to said inlet side of said membrane filter.

16. The device of claim 15 wherein said gas release control valve is connected to a measuring device which measures gas volume.

* * * * *